United States Patent
Dean et al.

(10) Patent No.: US 6,436,909 B1
(45) Date of Patent: Aug. 20, 2002

(54) ANTISENSE INHIBITION OF TRANSFORMING GROWTH FACTOR-β EXPRESSION

(75) Inventors: Nicholas M. Dean, Olivenhain; Susan F. Murray, Poway, both of CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/661,753

(22) Filed: Sep. 14, 2000

Related U.S. Application Data

(60) Provisional application No. 60/154,546, filed on Sep. 17, 1999.

(51) Int. Cl.$^7$ .......................... A61K 48/00; C12Q 1/68; C07H 21/02; C07H 21/04; C12N 15/85
(52) U.S. Cl. ............... 514/44; 435/6; 435/91.1; 435/91.3; 435/325; 435/375; 536/23.1; 536/23.2; 536/24.5; 536/24.3; 536/24.31; 536/24.33
(58) Field of Search .................. 435/6, 91.1, 91.3, 435/325, 375; 536/23.1, 23.2, 24.5, 24.3, 24.33, 24.31; 514/44

(56) References Cited

U.S. PATENT DOCUMENTS 5,683,988 A * 11/1997 Chung
5,801,154 A * 9/1998 Baracchini et al.

FOREIGN PATENT DOCUMENTS

| WO | WO 94/26888 |   | 11/1994 |
|----|-------------|---|---------|
| WO | WO 94/29452 | * | 12/1994 |
| WO | WO98/33904  | * | 8/1998  |
| WO | WO 99/30730 | * | 6/1999  |

OTHER PUBLICATIONS

Derynck et al., Nature, vol. 316, 1985, pp. 701–705.*
Andrea D.Branch, A Good Antisense Molecule is Hard to Find, Feb. 1998, TIBS 23, pp. 45–50.*
Kuang–Yu Jen et al, Suppression of Gene Expression by Targeted Disruption of Messenger RNA: Available Options and Current Strategies, Jul. 2000, Stem Cells, vol. 18, pp. 307–319.*
Douglas W. Green et al, Antisense Oligonucleotides: An Evoling Technology for the Modulation of Gene Expression in Human Disease, Jul. 2000, vol. 191, pp. 93–105.*
Arteaga et al., "Reversal of Tamoxifen Resistance of Human Breast Carcinomas In Vivo by Neutralizing Antibodies to Transforming Growth Factor–β", 1999 *J. Nat. Cancer Inst.* 91, 46–53.
Hoffman et al., "Potential Role of TGF–β Diabetic nephropathy", 1998 *Electrolyte Metab.* 24, 190–196.
Kim et al., "Inhibition of Wound–Induced Expression of Transforming Growth Factor–β1 mRNA by its Antisense Oligonucleotides", 1998 *Pharmacol. Res.* 37, 289–293.
Kim et al., "Role of TGF–β1 on the IgE–Dependent Anaphylaxis Reaction", 1999 *J. Immunol.* 162 4960–4965.
Liu et al., "The Transcription Factor EGR–1 Suppresses Transformation of Human Fibrosarcoma HT1080 Cells by Coordinated Induction of Transforming Growth Factor–β1, Fibronectin, and Plasminogen Activator Inhibitor–1*" 1999 *J. Biol. Chem.* 274, 4400–4411.
Nakajima et al., "An Autocrine Function for Transforming Growth Factor (TGF)–β3 in the Transformation of Atrioventricular Canal Endocardium into Mesenchyme during Chick Heart Development", 1998 *Japan Dev. Biol.* 194, 99–113.
Schüftan et al., "$α_2$–Macroglobulin reduces paracrine–and autocrine–stimulated matrix synthesis of cultured rat hepatic stellate cells", 1999 *Eur. J. Clin. Invest.* 29, 519–528.
Shen et al., "Inhibition of Transforming Growth Factor–β2 Expression with Phosphorothioate Antisense Oligonucleotides in U937 Cells", 1999 *Bioorg. Med. Chem.* 9, 13–18.
Tzai et al., "Antisense Oligonucleotide Specific for Transforming Growth of MBT–2 Factor–β1 Inhibit Both in Vitro and in Vivo Growth of MBT–2 Murine Bladder Cancer", 1998 *Anticancer Res.* 18, 1585–1589.

* cited by examiner

*Primary Examiner*—Andrew Wang
*Assistant Examiner*—Karen Lacourciere
(74) *Attorney, Agent, or Firm*—Licata & Tyrrell P.C.

(57) ABSTRACT

Compositions and methods are provided for modulating the expression of TGF-β. Antisense compounds, particularly antisense oligonucleotides, targeted to nucleic acids encoding TGF-β are preferred. Methods of using these compounds for modulation of TGF-β expression and for treatment of diseases associated with expression of TGF-β are also provided. Methods of sensitizing cells to apoptotic stimuli are also provided.

14 Claims, No Drawings

SEQUENCE LISTING

<160> NUMBER OF SEQ ID NOS: 68

<210> SEQ ID NO 1
<211> LENGTH: 2094
<212> TYPE: DNA
<213> ORGANISM: Mus musculus
<220> FEATURE:
<221> NAME/KEY: CDS
<222> LOCATION: (868)...(2040)

<400> SEQUENCE: 1

| | |
|---|---:|
| cgccgccgcc gccgcccttc gcgccccagg ccgtccccct cctcctcccg ccgcggatcc | 60 |
| tccagacagc caggcccccg gccggggcag ggggacgcc ccttcggggc accccggct | 120 |
| ctgagccgca ctcggagtcg gcctccgctg ggagccggca aggagcagc cgaggagccg | 180 |
| tccgaggccc cagagtctga gaccagccgc cgccgcaggg aggaggggga ggaggagtgg | 240 |
| gaggagggac gagctggttg agagaagagg aaaaaagttt tgagactttt ccgctgctac | 300 |
| tgcaagtcag agacgtgggg acttcttggc actgcgctgt ctcgcaagga ggcaggacct | 360 |
| gaggactcca gacagccctg ctcaccgtcg tggacactcg atcgctaccc ggcgttcctc | 420 |
| agacgcccct attccggacc agccctcggg agccacaaac cccgcctccc gcgaagactt | 480 |
| caccccaaag ctggggcgca ccccttgcac gccgccctcc cccagcctg cctcttgagt | 540 |
| ccctcgcatc ccaggaccct ctctccccg agaggcagat ctccctcgga cctgctggca | 600 |
| gtagctcccc tatttaagaa caccactttt tggatctcag agagcgctca tctcgatttt | 660 |
| taccctggtg gtatactgag acaccttggt gtcagagcct caccgcgact cctgctgctt | 720 |
| tctccctcaa cctcaaatta ttcaggacta tcacctacct ttccttggga daccccaccc | 780 |
| cacaagccct gcagggggcgg ggcctccgca tcccaccttt gccgagggtt ccgctctcc | 840 |
| gaagtgccgt ggggcgccgc ctccccc atg ccg ccc tcg ggg ctg cgg cta ctg | 894 |
|                                             Met Pro Pro Ser Gly Leu Arg Leu Leu<br>                                             1               5 | |
| ccg ctt ctg ctc cca ctc ccg tgg ctt cta gtg ctg acg ccc ggg agg<br>Pro Leu Leu Leu Pro Leu Pro Trp Leu Leu Val Leu Thr Pro Gly Arg<br> 10                    15                    20                    25 | 942 |
| cca gcc gcg gga ctc tcc acc tgc aag acc atc gac atg gag ctg gtg<br>Pro Ala Ala Gly Leu Ser Thr Cys Lys Thr Ile Asp Met Glu Leu Val<br>                  30                    35                        40 | 990 |
| aaa cgg aag cgc atc gaa gcc atc cgt ggc cag atc ctg tcc aaa cta<br>Lys Arg Lys Arg Ile Glu Ala Ile Arg Gly Gln Ile Leu Ser Lys Leu<br>                 45                    50                    55 | 1038 |
| agg ctc gcc agt ccc cca agc cag ggg gag gta ccg ccc ggc ccg ctg<br>Arg Leu Ala Ser Pro Pro Ser Gln Gly Glu Val Pro Pro Gly Pro Leu<br>            60                    65                    70 | 1086 |
| ccc gag gcg gtg ctc gct ttg tac aac agc acc cgc gac cgg gtg gca<br>Pro Glu Ala Val Leu Ala Leu Tyr Asn Ser Thr Arg Asp Arg Val Ala<br> 75                    80                    85 | 1134 |
| ggc gag agc gcc gac cca gag ccg gag ccc gaa gcg gac tac tat gct<br>Gly Glu Ser Ala Asp Pro Glu Pro Glu Pro Glu Ala Asp Tyr Tyr Ala<br> 90                    95                    100                   105 | 1182 |
| aaa gag gtc acc cgc gtg cta atg gtg gac cgc aac aac gcc atc tat<br>Lys Glu Val Thr Arg Val Leu Met Val Asp Arg Asn Asn Ala Ile Tyr<br>               110                   115                   120 | 1230 |
| gag aaa acc aaa gac atc tca cac agt ata tat atg ttc ttc aat acg<br>Glu Lys Thr Lys Asp Ile Ser His Ser Ile Tyr Met Phe Phe Asn Thr<br>             125                    130                    135 | 1278 |
| tca gac att cgg gaa gca gtg ccc gaa ccc cca ttg ctg tcc cgt gca | 1326 |

```
Ser Asp Ile Arg Glu Ala Val Pro Glu Pro Pro Leu Leu Ser Arg Ala
        140                 145                 150 gag ctg cgc ttg cag aga tta aaa tca gtg gag caa cat gtg gaa       1374
Glu Leu Arg Leu Gln Arg Leu Lys Ser Ser Val Glu Gln His Val Glu
155                 160                 165 ctc tac cag aaa tat agc aac aat tcc tgg cgt tac ctt ggt aac cgg   1422
Leu Tyr Gln Lys Tyr Ser Asn Asn Ser Trp Arg Tyr Leu Gly Asn Arg
170                 175                 180                 185 ctg ctg acc ccc act gat acg cct gag tgg ctg tct ttt gac gtc act   1470
Leu Leu Thr Pro Thr Asp Thr Pro Glu Trp Leu Ser Phe Asp Val Thr
                190                 195                 200 gga gtt gta cgg cag tgg ctg aac caa gga gac gga ata cag ggc ttt   1518
Gly Val Val Arg Gln Trp Leu Asn Gln Gly Asp Gly Ile Gln Gly Phe
            205                 210                 215 cga ttc agc gct cac tgc tct tgt gac agc aaa gat aac aaa ctc cac   1566
Arg Phe Ser Ala His Cys Ser Cys Asp Ser Lys Asp Asn Lys Leu His
        220                 225                 230 gtg gaa atc aac ggg atc agc ccc aaa cgt cgg ggc gac ctg ggc acc   1614
Val Glu Ile Asn Gly Ile Ser Pro Lys Arg Arg Gly Asp Leu Gly Thr
235                 240                 245 atc cat gac atg aac cgg ccc ttc ctc ctc atg gcc acc ccc ctg       1662
Ile His Asp Met Asn Arg Pro Phe Leu Leu Met Ala Thr Pro Leu
250                 255                 260                 265 gaa agg gcc cag cac ctg cac agc tca cgg cac cgg aga gcc ctg gat   1710
Glu Arg Ala Gln His Leu His Ser Ser Arg His Arg Arg Ala Leu Asp
                270                 275                 280 acc aac tat tgc ttc agc tcc aca gag aag aac tgt tgt gtg cgg cag   1758
Thr Asn Tyr Cys Phe Ser Ser Thr Glu Lys Asn Cys Cys Val Arg Gln
            285                 290                 295 ctg tac att gac ttt agg aag gac ctg ggt tgg aag tgg atc cac gag   1806
Leu Tyr Ile Asp Phe Arg Lys Asp Leu Gly Trp Lys Trp Ile His Glu
        300                 305                 310 ccc aag ggc tac cat gcc aac ttc tgt ctg gga ccc tgc ccc tat att   1854
Pro Lys Gly Tyr His Ala Asn Phe Cys Leu Gly Pro Cys Pro Tyr Ile
315                 320                 325 tgg agc ctg gac aca cag tac agc aag gtc ctt gcc ctc tac aac caa   1902
Trp Ser Leu Asp Thr Gln Tyr Ser Lys Val Leu Ala Leu Tyr Asn Gln
330                 335                 340                 345 cac aac ccg ggc gct tcg gcg tca ccg tgc tgc gtg ccg cag gct ttg   1950
His Asn Pro Gly Ala Ser Ala Ser Pro Cys Cys Val Pro Gln Ala Leu
                350                 355                 360 gag cca ctg ccc atc gtc tac tac gtg ggt cgc aag ccc aag gtg gag   1998
Glu Pro Leu Pro Ile Val Tyr Tyr Val Gly Arg Lys Pro Lys Val Glu
            365                 370                 375 cag ttg tcc aac atg att gtg cgc tcc tgc aag tgc agc tga           2040
Gln Leu Ser Asn Met Ile Val Arg Ser Cys Lys Cys Ser
        380                 385                 390 agccccgccc cgccccgccc ctcccggcag gcccggcccc gcccccgccc cgcc       2094

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
tgtctggagg atccgcggcg                                              20

<210> SEQ ID NO 3
```

-continued

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 3
tgctcctttg ccggctccca                                              20

<210> SEQ ID NO 4
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 4
cgagacagcg cagtgccaag                                              20

<210> SEQ ID NO 5
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 5
ggctcccgag ggctggtccg                                              20

<210> SEQ ID NO 6
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 6
gcaggagtcg cggtgaggct                                              20

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
aaaggtggga tgcggaggcc                                              20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
cagtagccgc agccccgagg                                              20

<210> SEQ ID NO 9
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 9
```

```
agtcccgcgg ctggcctccc                                               20

<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10
ggcttcgatg cgcttccgtt                                               20

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11
ggcggtacct ccccctggct                                               20

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
cgcctgccac ccggtcgcgg                                               20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
gtccaccatt agcacgcggg                                               20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
ggcactgctt cccgaatgtc                                               20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
gtcagcagcc ggttaccaag                                               20

<210> SEQ ID NO 16
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 16
agtgagcgct gaatcgaaag                                                      20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
gatggtgccc aggtcgcccc                                                      20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
aggagcagga agggccggtt                                                      20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
tccggtgccg tgagctgtgc                                                      20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gcccttgggc tcgtggatcc                                                      20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
cgcccgggtt gtgttggttg                                                      20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ggcttgcgac ccacgtagta                                                      20
```

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ggcgggcttt cagctgcact                                           20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ccacgtagta gacgatgggc                                           20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gtccaccatt agcacgcggg                                           20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
gtccaccatt agcacgcggg                                           20

<210> SEQ ID NO 27
<211> LENGTH: 1585
<212> TYPE: DNA
<213> ORGANISM: Rattus norvegicus
<220> FEATURE:
<221> NAME/KEY: CDS
<222> LOCATION: (413)...(1585)

<400> SEQUENCE: 27
accgcctccc gcaaagactt caccccaaag ctggggcgca ccccttgcac gccaccctcc    60
ccccagcctg cttcttgagt cccccgcatc caggaccct ctctcctctg ggaggccgat   120
ctccctcgga cctgctggca atagcttcct atttaagaac accccacttt tgggtcccag   180
agagcgctca tctcgatttt tatcccggtg gcatactgag acactctggt gtcagagcgt   240
caccgcgact cctgctgctt tctccctcaa cctcaaatta ttcaggacta tcacctacct   300
ttccttggga gaccccaccc caccccacaa gccctgcagg ggcgggcct ccgcatccca   360 cctttgcccg gggttcgcgc tctccgaagt tccgtgggc gccgcctccc cc atg ccg   418
                                                         Met Pro
                                                           1 ccc tcg ggg ctg cgg ctg ctg ccg ctt ctg ctc cca ctc ccg tgg ctt    466
Pro Ser Gly Leu Arg Leu Leu Pro Leu Leu Leu Pro Leu Pro Trp Leu
           5                  10                  15

| | | |
|---|---|---|
| cta gtg ctg acg ccc ggg agg cca gcc gcg gga ctc tcc acc tgc aag<br>Leu Val Leu Thr Pro Gly Arg Pro Ala Ala Gly Leu Ser Thr Cys Lys<br>20                      25                      30 | | 514 |
| acc atc gac atg gag ctg gtg aaa cgg aag cgc atc gaa gcc atc cgt<br>Thr Ile Asp Met Glu Leu Val Lys Arg Lys Arg Ile Glu Ala Ile Arg<br>35                    40                    45                  50 | | 562 |
| ggc cag atc ctg tcc aaa cta agg ctc gcc agt ccc ccg agc cag ggg<br>Gly Gln Ile Leu Ser Lys Leu Arg Leu Ala Ser Pro Pro Ser Gln Gly<br>55                    60                    65 | | 610 |
| gag gta ccg ccg ggc ccg ctg ccc gag gcg gtg ctc gct ttg tac aac<br>Glu Val Pro Pro Gly Pro Leu Pro Glu Ala Val Leu Ala Leu Tyr Asn<br>70                    75                    80 | | 658 |
| agc acc cgc gac cgg gtg gca ggc gag agc gct gac ccg gag ccc gag<br>Ser Thr Arg Asp Arg Val Ala Gly Glu Ser Ala Asp Pro Glu Pro Glu<br>85                    90                    95 | | 706 |
| ccc gag gcg gac tac tac gcc aaa gaa gtc acc cgc gtg cta atg gtg<br>Pro Glu Ala Asp Tyr Tyr Ala Lys Glu Val Thr Arg Val Leu Met Val<br>100                  105                110 | | 754 |
| gac cgc aac aac gca atc tat gac aaa acc aaa gac atc aca cac agt<br>Asp Arg Asn Asn Ala Ile Tyr Asp Lys Thr Lys Asp Ile Thr His Ser<br>115                120                125                130 | | 802 |
| ata tat atg ttc ttc aat acg tca gac att cgg gaa gca gtg cca gaa<br>Ile Tyr Met Phe Phe Asn Thr Ser Asp Ile Arg Glu Ala Val Pro Glu<br>135                140                145 | | 850 |
| ccc cca ttg ctg tcc cgt gca gag ctg cgc ctg cag aga ttc aag tca<br>Pro Pro Leu Leu Ser Arg Ala Glu Leu Arg Leu Gln Arg Phe Lys Ser<br>150                  155                160 | | 898 |
| act gtg gag caa cac gta gaa ctc tac cag aaa tat agc aac aat tcc<br>Thr Val Glu Gln His Val Glu Leu Tyr Gln Lys Tyr Ser Asn Asn Ser<br>165                170                175 | | 946 |
| tgg cgt tac ctt ggt aac cgg ctg ctg acc ccc act gat acg cct gag<br>Trp Arg Tyr Leu Gly Asn Arg Leu Leu Thr Pro Thr Asp Thr Pro Glu<br>180                185                190 | | 994 |
| tgg ctg tct ttt gac gtc act gga gtt gtc cgg cag tgg ctg aac caa<br>Trp Leu Ser Phe Asp Val Thr Gly Val Val Arg Gln Trp Leu Asn Gln<br>195                200                205                210 | | 1042 |
| gga gac gga ata cag ggc ttt cgc ttc agt gct cac tgc tct tgt gac<br>Gly Asp Gly Ile Gln Gly Phe Arg Phe Ser Ala His Cys Ser Cys Asp<br>215                220                225 | | 1090 |
| agc aaa gat aat gta ctc cac gtg gaa atc aat ggg atc agt ccc aaa<br>Ser Lys Asp Asn Val Leu His Val Glu Ile Asn Gly Ile Ser Pro Lys<br>230                235                240 | | 1138 |
| cgt cga ggt gac ctg ggc acc atc cat gac atg aac cga ccc ttc ctg<br>Arg Arg Gly Asp Leu Gly Thr Ile His Asp Met Asn Arg Pro Phe Leu<br>245                250                255 | | 1186 |
| ctc ctc atg gcc acc ccc ctg gaa agg gct caa cac ctg cac agc tcc<br>Leu Leu Met Ala Thr Pro Leu Glu Arg Ala Gln His Leu His Ser Ser<br>260                265                270 | | 1234 |
| agg cac cgg aga gcc ctg gat acc aac tac tgc ttc agc tcc aca gag<br>Arg His Arg Arg Ala Leu Asp Thr Asn Tyr Cys Phe Ser Ser Thr Glu<br>275                280                285                290 | | 1282 |
| aag aac tgc tgt gta cgg cag ctg tac att gac ttt agg aag gac ctg<br>Lys Asn Cys Cys Val Arg Gln Leu Tyr Ile Asp Phe Arg Lys Asp Leu<br>295                300                305 | | 1330 |
| ggt tgg aag tgg atc cac gag ccc aag ggc tac cat gcc aac ttc tgt<br>Gly Trp Lys Trp Ile His Glu Pro Lys Gly Tyr His Ala Asn Phe Cys<br>310                315                320 | | 1378 |
| ctg ggg ccc tgc ccc tac att tgg agc ctg gac aca cag tac agc aag<br>Leu Gly Pro Cys Pro Tyr Ile Trp Ser Leu Asp Thr Gln Tyr Ser Lys | | 1426 |

-continued

```
              325                 330                 335
gtc ctt gcc ctc tac aac caa cac aac ccg ggt gct tcc gca tca ccg      1474
Val Leu Ala Leu Tyr Asn Gln His Asn Pro Gly Ala Ser Ala Ser Pro
            340                 345                 350 tgc tgc gtg ccg cag gct ttg gag cca ctg ccc atc gtc tac tac gtg      1522
Cys Cys Val Pro Gln Ala Leu Glu Pro Leu Pro Ile Val Tyr Tyr Val
355                 360                 365                 370 ggt cgc aag ccc aag gtg gag cag ttg tcc aac atg atc gtg cgc tcc      1570
Gly Arg Lys Pro Lys Val Glu Gln Leu Ser Asn Met Ile Val Arg Ser
                375                 380                 385 tgc aag tgc agc tga                                                   1585
Cys Lys Cys Ser
            390

<210> SEQ ID NO 28
<211> LENGTH: 2745
<212> TYPE: DNA
<213> ORGANISM: Homo sapiens
<220> FEATURE:
<221> NAME/KEY: CDS
<222> LOCATION: (842)...(2017)

<400> SEQUENCE: 28
acctccctcc gcggagcagc cagacagcga gggccccggc cggggcagg  ggggacgccc      60 cgtccgggc  acccccccg  gctctgagcc gcccgcgggg ccggcctcgg cccggagcgg     120
aggaaggagt cgccgaggag cagcctgagg ccccagagtc tgagacgagc cgccgccgcc     180
cccgccactg cggggaggag gggaggagg  agcgggagga gggacgagct ggtcgggaga     240
agaggaaaaa aacttttgag acttttccgt tgccgctggg agccggaggc gcggggacct     300
cttggcgcga cgctgccccg cgaggaggca ggacttgggg accccagacc gcctcccttt     360
gccgccgggg acgcttgctc cctccctgcc ccctacacgg cgtccctcag gcgcccccat     420
tccggaccag ccctcgggag tcgccgaccc ggcctcccgc aaagactttt ccccagacct     480
cgggcgcacc ccctgcacgc cgccttcatc cccggcctgt ctcctgagcc cccgcgcatc     540 ctagacccctt tctcctccag gagacggatc tctctccgac ctgccacaga tcccctattc     600
aagaccaccc accttctggt accagatcgc gcccatctag gttatttccg tgggatactg     660
agacaccccc ggtccaagcc tcccctccac cactgcgccc ttctccctga ggagcctcag     720 cttttccctcg aggccctcct accttttgcc gggagacccc cagcccctgc aggggcgggg     780
cctccccacc acaccagccc tgttcgcgct ctcggcagtg ccggggggcg ccgcctcccc     840 c atg ccg ccc tcc ggg ctg cgg ctg ctg ccg ctg ctg cta ccg ctg ctg     889
  Met Pro Pro Ser Gly Leu Arg Leu Leu Pro Leu Leu Leu Pro Leu Leu
  1               5                  10                  15 tgg cta ctg gtg ctg acg cct ggc ccg ccg gcc gcg gga cta tcc acc       937
Trp Leu Leu Val Leu Thr Pro Gly Pro Pro Ala Ala Gly Leu Ser Thr
                20                  25                  30 tgc aag act atc gac atg gag ctg gtg aag cgg aag cgc atc gag gcc       985
Cys Lys Thr Ile Asp Met Glu Leu Val Lys Arg Lys Arg Ile Glu Ala
        35                  40                  45 atc cgc ggc cag atc ctg tcc aag ctg cgg ctc gcc agc ccc ccg agc      1033
Ile Arg Gly Gln Ile Leu Ser Lys Leu Arg Leu Ala Ser Pro Pro Ser
50                  55                  60 cag ggg gag gtg ccg ccc ggc ccg ctg ccc gag gcc gtg ctc gcc ctg      1081
Gln Gly Glu Val Pro Pro Gly Pro Leu Pro Glu Ala Val Leu Ala Leu
65                  70                  75                  80 tac aac agc acc cgc gac cgg gtg gcc ggg gag agt gca gaa ccg gag      1129
Tyr Asn Ser Thr Arg Asp Arg Val Ala Gly Glu Ser Ala Glu Pro Glu
```

-continued

| | 85 | | | | 90 | | | | 95 | | | | |
|---|---|---|---|---|---|---|---|---|---|---|---|---|---|
| ccc | gag | cct | gag | gcc | gac | tac | tac | gcc | aag | gag | gtc | acc | cgc | gtg | cta | 1177 |
| Pro | Glu | Pro | Glu | Ala | Asp | Tyr | Tyr | Ala | Lys | Glu | Val | Thr | Arg | Val | Leu | |
| | | | 100 | | | | | 105 | | | | | 110 | | | |

| atg | gtg | gaa | acc | cac | aac | gaa | atc | tat | gac | aag | ttc | aag | cag | agt | aca | 1225 |
| Met | Val | Glu | Thr | His | Asn | Glu | Ile | Tyr | Asp | Lys | Phe | Lys | Gln | Ser | Thr | |
| | | | 115 | | | | | 120 | | | | | 125 | | | |

| cac | agc | ata | tat | atg | ttc | ttc | aac | aca | tca | gag | ctc | cga | gaa | gcg | gta | 1273 |
| His | Ser | Ile | Tyr | Met | Phe | Phe | Asn | Thr | Ser | Glu | Leu | Arg | Glu | Ala | Val | |
| | | 130 | | | | | 135 | | | | | 140 | | | | |

| cct | gaa | ccc | gtg | ttg | ctc | tcc | cgg | gca | gag | ctg | cgt | ctg | ctg | agg | agg | 1321 |
| Pro | Glu | Pro | Val | Leu | Leu | Ser | Arg | Ala | Glu | Leu | Arg | Leu | Leu | Arg | Arg | |
| 145 | | | | | 150 | | | | | 155 | | | | | 160 | |

| ctc | aag | tta | aaa | gtg | gag | cag | cac | gtg | gag | ctg | tac | cag | aaa | tac | agc | 1369 |
| Leu | Lys | Leu | Lys | Val | Glu | Gln | His | Val | Glu | Leu | Tyr | Gln | Lys | Tyr | Ser | |
| | | | | 165 | | | | | 170 | | | | | 175 | | |

| aac | aat | tcc | tgg | cga | tac | ctc | agc | aac | cgg | ctg | ctg | gca | ccc | agc | gac | 1417 |
| Asn | Asn | Ser | Trp | Arg | Tyr | Leu | Ser | Asn | Arg | Leu | Leu | Ala | Pro | Ser | Asp | |
| | | | 180 | | | | | 185 | | | | | 190 | | | |

| tcg | cca | gag | tgg | tta | tct | ttt | gat | gtc | acc | gga | gtt | gtg | cgg | cag | tgg | 1465 |
| Ser | Pro | Glu | Trp | Leu | Ser | Phe | Asp | Val | Thr | Gly | Val | Val | Arg | Gln | Trp | |
| | | 195 | | | | | 200 | | | | | 205 | | | | |

| ttg | agc | cgt | gga | ggg | gaa | att | gag | ggc | ttt | cgc | ctt | agc | gcc | cac | tgc | 1513 |
| Leu | Ser | Arg | Gly | Gly | Glu | Ile | Glu | Gly | Phe | Arg | Leu | Ser | Ala | His | Cys | |
| | 210 | | | | | 215 | | | | | 220 | | | | | |

| tcc | tgt | gac | agc | agg | gat | aac | aca | ctg | caa | gtg | gac | atc | aac | ggg | ttc | 1561 |
| Ser | Cys | Asp | Ser | Arg | Asp | Asn | Thr | Leu | Gln | Val | Asp | Ile | Asn | Gly | Phe | |
| 225 | | | | | 230 | | | | | 235 | | | | | 240 | |

| act | acc | ggc | cgc | cga | ggt | gac | ctg | gcc | acc | att | cat | ggc | atg | aac | cgg | 1609 |
| Thr | Thr | Gly | Arg | Arg | Gly | Asp | Leu | Ala | Thr | Ile | His | Gly | Met | Asn | Arg | |
| | | | | 245 | | | | | 250 | | | | | 255 | | |

| cct | ttc | ctg | ctt | ctc | atg | gcc | acc | ccg | ctg | gag | agg | gcc | cag | cat | ctg | 1657 |
| Pro | Phe | Leu | Leu | Leu | Met | Ala | Thr | Pro | Leu | Glu | Arg | Ala | Gln | His | Leu | |
| | | | | 260 | | | | | 265 | | | | | 270 | | |

| caa | agc | tcc | cgg | cac | cgc | cga | gcc | ctg | gac | acc | aac | tat | tgc | ttc | agc | 1705 |
| Gln | Ser | Ser | Arg | His | Arg | Arg | Ala | Leu | Asp | Thr | Asn | Tyr | Cys | Phe | Ser | |
| | | | 275 | | | | | 280 | | | | | 285 | | | |

| tcc | acg | gag | aag | aac | tgc | tgc | gtg | cgg | cag | ctg | tac | att | gac | ttc | cgc | 1753 |
| Ser | Thr | Glu | Lys | Asn | Cys | Cys | Val | Arg | Gln | Leu | Tyr | Ile | Asp | Phe | Arg | |
| | | 290 | | | | | 295 | | | | | 300 | | | | |

| aag | gac | ctc | ggc | tgg | aag | tgg | atc | cac | gag | ccc | aag | ggc | tac | cat | gcc | 1801 |
| Lys | Asp | Leu | Gly | Trp | Lys | Trp | Ile | His | Glu | Pro | Lys | Gly | Tyr | His | Ala | |
| 305 | | | | | 310 | | | | | 315 | | | | | 320 | |

| aac | ttc | tgc | ctc | ggg | ccc | tgc | ccc | tac | att | tgg | agc | ctg | gac | acg | cag | 1849 |
| Asn | Phe | Cys | Leu | Gly | Pro | Cys | Pro | Tyr | Ile | Trp | Ser | Leu | Asp | Thr | Gln | |
| | | | | 325 | | | | | 330 | | | | | 335 | | |

| tac | agc | aag | gtc | ctg | gcc | ctg | tac | aac | cag | cat | aac | ccg | ggc | gcc | tcg | 1897 |
| Tyr | Ser | Lys | Val | Leu | Ala | Leu | Tyr | Asn | Gln | His | Asn | Pro | Gly | Ala | Ser | |
| | | | 340 | | | | | 345 | | | | | 350 | | | |

| gcg | gcg | ccg | tgc | tgc | gtg | ccg | cag | gcg | ctg | gag | ccg | ctg | ccc | atc | gtg | 1945 |
| Ala | Ala | Pro | Cys | Cys | Val | Pro | Gln | Ala | Leu | Glu | Pro | Leu | Pro | Ile | Val | |
| | | 355 | | | | | 360 | | | | | 365 | | | | |

| tac | tac | gtg | ggc | cgc | aag | ccc | aag | gtg | gag | cag | ctg | tcc | aac | atg | atc | 1993 |
| Tyr | Tyr | Val | Gly | Arg | Lys | Pro | Lys | Val | Glu | Gln | Leu | Ser | Asn | Met | Ile | |
| | 370 | | | | | 375 | | | | | 380 | | | | | |

| gtg | cgc | tcc | tgc | aag | tgc | agc | tga | ggtcccgccc | cgccccgccc | cgccccggca | | | | | | 2047 |
| Val | Arg | Ser | Cys | Lys | Cys | Ser | | | | | | | | | | |
| 385 | | | | | 390 | | | | | | | | | | | | ggcccggccc caccccgccc cgccccgct gccttgccca tggggctgt atttaaggac 2107

```
accgtgcccc aagcccacct ggggccccat taaagatgga gagaggactg cggatctctg    2167
tgtcattggg cgcctgcctg gggtctccat ccctgacgtt cccccactcc cactccctct    2227
ctctccctct ctgcctcctc ctgcctgtct gcactattcc tttgcccggc atcaaggcac    2287 agggaccag tggggaacac tactgtagtt agatctattt attgagcacc ttgggcactg     2347
ttgaagtgcc ttacattaat gaactcattc agtcaccata gcaacactct gagatggcag    2407
ggactctgat aacacccatt ttaaaggttg aggaaacaag cccagagagg ttaagggagg    2467
agttcctgcc caccaggaac ctgctttagt gggggatagt gaagaagaca ataaaagata    2527
gtagttcagg ccaggcgggg tgctcacgcc tgtaatccta gcacttttgg gaggcagaga    2587
tgggaggata cttgaatcca ggcatttgag accagcctgg gtaacatagt gagaccctat    2647
ctctacaaaa cacttttaaa aaatgtacac ctgtggtccc agctactctg gaggctaagg    2707
tgggaggatc acttgatcct gggaggtcaa ggctgcag                            2745
```

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29

```
cgactccttc ctccgctccg                                                20
```

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30

```
ctcgtccctc ctcccgctcc                                                20
```

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31

```
aagtcctgcc tcctcgcggg                                                20
```

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32

```
aagggtctag gatgcgcggg                                                20
```

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 33
ctcagggaga agggcgcagt                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
gcactgccga gagcgcgaac                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gtagcagcag cggcagcagc                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
atggcctcga tgcgcttccg                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gcgtagtagt cggcctcagg                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
accactgccg cacaactccg                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tcggcggccg gtagtgaacc                                              20

<210> SEQ ID NO 40
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 40
gaagttggca tggtagccct                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ggcgcccggg ttatgctggt                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ctccaccttg ggcttgcggc                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
aatgacacag agatccgcag                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
tagatctaac tacagtagtg                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
cgcctggcct gaactactat                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
```

```
cccaggctgg tctcaaatgc                                                 20

<210> SEQ ID NO 47
<211> LENGTH: 4267
<212> TYPE: DNA
<213> ORGANISM: Mus musculus
<220> FEATURE:
<221> NAME/KEY: CDS
<222> LOCATION: (1218)...(2462)

<400> SEQUENCE: 47
ggttatctgc tggcagcagg tttgctcgga gcagagctgc tgaaactgcc ggcaggagag     60
cgagtgggag agaaagagag aaggcgctga gagctgagct ctggggcagg cgtcagggat    120
ggagagaagt attagggttt aaagagccat tctggagcaa cccatctgcg gagagaagga    180
tcggcagagg tctattttag ggtcgcaagt acctacttac cctaagcgag aaagtgcaac    240
cttggtggaa gctaggagaa gctagggaag ggtgcgagtc ccggggcagc ccgcagccaa    300
cgcgcccagg aggcggtgtt gttccacagg ggttaaggag gtggccgatc gctgtcgccc    360
ttggccgcct ggagcaagaa aaggaggatc tgaaggaccg agctggaggc tggccctctt    420
tgcaggcagc agcggcggct gcaacgtgga gcgacccagc cgggtgtagg ccacagcgcg    480 ccggcagga gcgggatcct cgccgcctgc tccggcctct gtggatctcc ggggcggaca     540
gtatcccacc gagtctccga gtgagccgct ccggggcgca tctgcctccc cgcggctcgc    600
caggctcgcc ctcggcgcgc gcgcacgcac gcgcgcacac gcgcacacat ccacacgcac    660
actcatccac acacgtgtgg aaggcagggc cgagccgctc ggtctttgaa cttctcagtt    720
agagcccggc gcagccccgg ccgccgctca gcgctccccg cggccctgcg tgcctcctgc    780
cagcccccgg accttctcgt tcgtcccttt tggccggag atcggagtt cagatcagcc      840 actccgcacc gagcctgaca cactgaactc catttcttcc tcttaagttt atttctactt    900
cagagccact caccctctcc cttccaggag aaaaaaaaaa caaacctttc ttactcctta    960
aagtgagaga ttccccccc accccgcccc agcatcgcat attaatatct ccacgttggg    1020
aacgcgttgc atttctttt ttaaaggaat cccagccagg aacgtttttc tattgggcat    1080
taactttcga ctgctttgca aaagtttcgt attaaagaac aactctacct gaccgctctg   1140
agaattacta gtttcttttt tatatatatt ttttcttact ttaaataaca acatcaacgt   1200
ttcttccttt taaaaac atg cac tac tgt gtg ctg agc acc ttt ttg ctc      1250
                    Met His Tyr Cys Val Leu Ser Thr Phe Leu Leu
                     1               5                      10 ctg cat ctg gtc ccg gtg gcg ctc agt ctg tct acc tgc agc acc ctc     1298
Leu His Leu Val Pro Val Ala Leu Ser Leu Ser Thr Cys Ser Thr Leu
              15                  20                  25 gac atg gat cag ttt atg cgc aag agg atc gag gcc atc cgc ggg cag     1346
Asp Met Asp Gln Phe Met Arg Lys Arg Ile Glu Ala Ile Arg Gly Gln
         30                  35                  40 atc ctg agc aag ctg aag ctc acc agc ccc ccg gaa gac tat ccg gag     1394
Ile Leu Ser Lys Leu Lys Leu Thr Ser Pro Pro Glu Asp Tyr Pro Glu
     45                  50                  55 ccg gat gag gtc ccc ccg gag gtg att tcc atc tac aac agt acc agg     1442
Pro Asp Glu Val Pro Pro Glu Val Ile Ser Ile Tyr Asn Ser Thr Arg
 60                  65                  70                  75 gac tta ctg cag gag aag gca agc cgg agg gca gcc gcc tgc gag cgc     1490
Asp Leu Leu Gln Glu Lys Ala Ser Arg Arg Ala Ala Ala Cys Glu Arg
                 80                  85                  90 gag cgg agc gag cag gag tac tac gcc aag gag gtt tat aaa atc gac     1538
Glu Arg Ser Glu Gln Glu Tyr Tyr Ala Lys Glu Val Tyr Lys Ile Asp
```

-continued

```
                        95                  100                 105
atg ccg tcc cac ctc ccc tcc gaa aat gcc atc ccg ccc act ttc tac    1586
Met Pro Ser His Leu Pro Ser Glu Asn Ala Ile Pro Pro Thr Phe Tyr
        110                 115                 120 aga ccc tac ttc aga atc gtc cgc ttt gat gtc tca aca atg gag aaa    1634
Arg Pro Tyr Phe Arg Ile Val Arg Phe Asp Val Ser Thr Met Glu Lys
    125                 130                 135 aat gct tcg aat ctg gtg aag gca gag ttc agg gtc ttc cgc ttg caa    1682
Asn Ala Ser Asn Leu Val Lys Ala Glu Phe Arg Val Phe Arg Leu Gln
140                 145                 150                 155 aac ccc aaa gcc aga gtg gcc gag cag cgg att gaa ctg tat cag atc    1730
Asn Pro Lys Ala Arg Val Ala Glu Gln Arg Ile Glu Leu Tyr Gln Ile
                160                 165                 170 ctt aaa tcc aaa gac tta aca tct ccc acc cag cgc tac atc gat agc    1778
Leu Lys Ser Lys Asp Leu Thr Ser Pro Thr Gln Arg Tyr Ile Asp Ser
        175                 180                 185 aag gtt gtg aaa acc aga gcg gag ggt gaa tgg ctc tcc ttc gac gtg    1826
Lys Val Val Lys Thr Arg Ala Glu Gly Glu Trp Leu Ser Phe Asp Val
    190                 195                 200 aca gac gct gtg cag gag tgg ctt cac cac aaa gac agg aac ctg ggg    1874
Thr Asp Ala Val Gln Glu Trp Leu His His Lys Asp Arg Asn Leu Gly
205                 210                 215 ttt aaa ata agt tta cac tgc ccc tgc tgt acc ttc gtg ccg tct aat    1922
Phe Lys Ile Ser Leu His Cys Pro Cys Cys Thr Phe Val Pro Ser Asn
220                 225                 230                 235 aat tac atc atc ccg aat aaa agc gaa gag ctc gag gcg aga ttt gca    1970
Asn Tyr Ile Ile Pro Asn Lys Ser Glu Glu Leu Glu Ala Arg Phe Ala
                240                 245                 250 ggt att gat ggc acc tct aca tat gcc agt ggt gat cag aaa act ata    2018
Gly Ile Asp Gly Thr Ser Thr Tyr Ala Ser Gly Asp Gln Lys Thr Ile
        255                 260                 265 aag tcc act agg aaa aaa acc agt ggg aag acc cca cat ctc ctg cta    2066
Lys Ser Thr Arg Lys Lys Thr Ser Gly Lys Thr Pro His Leu Leu Leu
    270                 275                 280 atg ttg ttg ccc tcc tac aga ctg gag tca caa cag tcc agc cgg cgg    2114
Met Leu Leu Pro Ser Tyr Arg Leu Glu Ser Gln Gln Ser Ser Arg Arg
285                 290                 295 aag aag cgc gct ttg gat gct gcc tac tgc ttt aga aat gtg cag gat    2162
Lys Lys Arg Ala Leu Asp Ala Ala Tyr Cys Phe Arg Asn Val Gln Asp
300                 305                 310                 315 aat tgc tgc ctt cgc cct ctt tac att gat ttt aag agg gat ctt gga    2210
Asn Cys Cys Leu Arg Pro Leu Tyr Ile Asp Phe Lys Arg Asp Leu Gly
                320                 325                 330 tgg aaa tgg atc cat gaa ccc aaa ggg tac aat gct aac ttc tgt gct    2258
Trp Lys Trp Ile His Glu Pro Lys Gly Tyr Asn Ala Asn Phe Cys Ala
        335                 340                 345 ggg gca tgc cca tat cta tgg agt tca gac act caa cac acc aaa gtc    2306
Gly Ala Cys Pro Tyr Leu Trp Ser Ser Asp Thr Gln His Thr Lys Val
    350                 355                 360 ctc agc ctg tac aac acc ata aat ccc gaa gct tcc gct tcc cct tgc    2354
Leu Ser Leu Tyr Asn Thr Ile Asn Pro Glu Ala Ser Ala Ser Pro Cys
365                 370                 375 tgt gtg tcc cag gat ctg gaa cca ctg acc att ctc tat tac att gga    2402
Cys Val Ser Gln Asp Leu Glu Pro Leu Thr Ile Leu Tyr Tyr Ile Gly
380                 385                 390                 395 aat acg ccc aag atc gaa cag ctt tcc aat atg att gtc aag tct tgt    2450
Asn Thr Pro Lys Ile Glu Gln Leu Ser Asn Met Ile Val Lys Ser Cys
                400                 405                 410 aaa tgc agc taa agtccttggg aaagccagga cacgaaaatc acggtgacaa        2502
Lys Cys Ser
```

-continued

Lys Cys Ser

```
tgacatataa tgacaacgat gacgaccatg atgtttgtga caggagggag ggagttttga    2562
ttcatcagtg tttaaaaaaa aaaaaattgg agaaaaaaaa tcggtactag ttcaaacatt    2622
ttgcaagctt gtgttctgtt tgttaaaact ggcatctgag attacagcaa caacaaccac    2682
aaaaatggaa ggcgttagtc tgcatctcac ctacttccta agagacacaa aaagaaaaca    2742
tctttttttt tttaaggaaa aaaataaaca ctggaagaat ttgttagtgt taattatgtg    2802
aaaaaaaaaa aacatcaaaa caaaacagga aaatccgttc agtggagttg tacgtattgt    2862
ttccagcccg catttcaccc cacgcctctc ctggttcctc tgtattgctc tctgcagtgg    2922
gtgccctccc cgtcccttcc tccaagctaa cagtgggtta tttattgtgt gttactatat    2982
aatgaacctt tcattaccct tggaaaacaa acaggtgta taaatcgaga ccaaatactt    3042
tgccacaaac tcatggatgg cttaaggagt ttgaactcaa ataagccagg gggaaggagg    3102
tcatagtgga tgacccctg tgagttgtta taggactaag caagtcttct gtggaaaaat     3162
caaagcccca gcaaacacgt gtctgccgaa gcttcatgga cgccatatgc ccagaaggcc    3222
tgttaacaaa gaaaacttgg aatcagtggc aatctggaag attttttttt cctttaatt     3282 gtaaatggtt ctttgccagt ttaagcaagc cggtgaaatg ttgacctgtt ttgatatgta    3342
ttgtcagact tttgaccgtg aagtggctgt tgatctacaa tacaggtttt cctttgtct     3402 tggtatatgt aattacatgg atactattaa aatagacggg tctagaagcc agcatgattg    3462
aaaacacact gcagatctgt ttttccaaac tattaaatcg aaacagtaac tactttacat    3522
gtaatgtgta gatcttacca cattttaat attctgtaat aatggttatg atttagattg      3582
aacttaaatt tggactttt tttttaatga tcattcagat tgtatatttg tttccttag       3642 ctggccagta cctttgaata aaaccctag atttgactt gcactacaaa ttcaattttt       3702
tttatatact atcttccctg cctgtattt atgtattgtc catttaatga catgagctac      3762
ctgggtccat tcctccccca accccagttc cttctatttt ccaaaagata aaaccaaag      3822 cccaaaaagc taggtttgag ctccacagtg tttcagcctt ttctgcgtca gtgtgagtca    3882
tgtggcgggt gagcggtggg gcttctggga tggatggttc tgtgtgaaca cagaagttcg    3942
cacaaatgta ggcttagcta gggtttaaga atctcaactc agagtcttag tgactgggct    4002
aggaaaagtt tctttaactc ctatatttat ggactctctt tgccgttcaa aagcagacag    4062
ttcaaaggaa gcacctttt ctttaattgg ttttttttggt gctcatgggg tgtattaaaa     4122
gacacacagt ttggttgagt ttttcaaagg gggaaaaagt ccaggccagc actcgtcatt    4182
ttattcataa tttcatccat tatttccctg atttcattga aatacaggtt ttgaaagaca    4242
ttctttgcag gctgattaaa aaaaa                                          4267
```

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
gccggcagtt tcagcagctc      20

<210> SEQ ID NO 49
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 49
ctcgcaccct tccctagctt                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
tttcttgctc caggcggcca                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gagcaggcgg cgaggatccc                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gccctgcctt ccacacgtgt                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
gtgcggagtg gctgatctga                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aaaatgcaac gcgttcccaa                                               20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ccgggaccag atgcaggagc                                               20
```

```
<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tccggcttgc cttctcctgc                                                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gggttttgca agcggaagac                                                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
cgatgtagcg ctgggtggga                                                    20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ggtcttccca ctggtttttt                                                    20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
aagcttcggg atttatggtg                                                    20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
accgtgattt tcgtgtcctg                                                    20

<210> SEQ ID NO 62
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 62
gcgggctgga aacaatacgt                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cccctggctt atttgagttc                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
accggcttgc ttaaactggc                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
cagccacttc acggtcaaaa                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
atggacccag gtagctcatg                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
cacccgccac atgactcaca                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
tacaccccat gagcaccaaa                                               20
```

ANTISENSE INHIBITION OF TRANSFORMING GROWTH FACTOR-β EXPRESSION

This application claims the benefit of U.S. Provisional Application No. 60/154,546 filed Sep. 17, 1999.

FIELD OF THE INVENTION

The present invention provides compositions and methods for modulating the expression of transforming growth factor-β (TGF-β). In particular, this invention relates to antisense compounds, particularly oligonucleotides, specifically hybridizable with nucleic acids encoding human TGF-β. Such oligonucleotides have been shown to modulate the expression of TGF-β.

BACKGROUND OF THE INVENTION

Transforming growth factor-β (TGF-β) is a cytokine which regulates biological processes such as cell proliferation, differentiation and immune reaction. It has been found to have many actions in tissue repair, stimulating the deposition of extracellular matrix in multiple ways. TGF-β stimulates the synthesis of matrix proteins including fibronectin, collagens and proteoglycans. It also blocks the degradation of matrix by inhibiting protease secretion and by inducing the expression of protease inhibitors. It also facilitates cell-matrix adhesion and matrix deposition via modulation of expression of integrin matrix receptors, and lastly TGF-β also upregulates its own expression. TGF-β exists in three isoforms in mammals: TGF-β1, -2 and -3. These function similarly in vitro.

Fibrosis is a pathological process, usually resulting from injury, which can occur in any organ. Excessive amounts of extracellular matrix accumulate within a tissue, forming scar tissue which causes dysfunction and, potentially, organ failure. Fibrosis can be either chronic or acute. Chronic fibrosis includes fibrosis of the major organs, most commonly liver, kidney and/or heart, and normally has a genetic or idiopathic origin. Progressive fibrosis of the kidney is the main cause of chronic renal disease. In diabetics, fibrosis within glomeruli (glomerulosclerosis) and between tubules (tubulointerstitial fibrosis) causes the progressive loss of renal function that leds to end-stage renal disease. Fibrotic lung disorders include some 180 different conditions and result in severe impairment of lung function.

Acute fibrosis is associated with injury, often as a result of surgery. Surgical adhesion represents the largest class of acute fibrosis. Surgery often results in excessive scarring and fibrous adhesions. It is estimated that over 90% of post-surgical patients are affected by adhesions. Abdominal adhesions can lead to small bowel obstruction and female infertility. Fibrosis after neck and back surgery (laminectomy, discectomy) can cause significant pain. Fibrosis after eye surgery can impair vision. Pericardial adhesions after coronary bypass surgery, fibrosis after organ transplant rejection and general scarring after plastic surgery are other examples. This represents a major unmet medical need.

Antisense and other inhibitors of TGF-β have been used to elucidate the role of TGF-βs in cancer, anaphylaxis, fibrosis and other conditions. As examples:

Dzau (WO 94/26888) discloses use of antisense sequences which inhibit the expression of cyclins and growth factors including TGF-β$_1$, TGF, bFGF, PDGF for inhibiting vascular cellular activity of cells associated with vascular lesion formation in mammals.

Shen et al. discloses use of phosphorothioate antisense oligonucleotides targeted to TGF-β2 to reduce TGF-β2 expression in U937 cells (Bioorg. Med. Chem. Lett., 1999, 9, 13–18).

Schuftan et al. (1999, *Eur. J. Clin Invest.*, 29, 519–528) disclose use of a2-macroglobin or antisense to TGF-β1 to reduce extracellular matrix synthesis in cultured rat hepatic stellate cells.

Kim et al. have used antisense oligonucleotides targeted to TGF-β1 to inhibit passive cutaneous anaphylaxis and histamine release. 1999, *J. Immunol.* 162, 4960–4965.

Kim et al. have also used an antisense TGF-β1 oligodeoxynucleotide to inhibit wound-induced expression of TGF-β1 mRNA in mouse skin. Pharmacol. Res., 1998, 37, 289–293.

Liu et al. used TGF-β antibody or antisense to TGF-β1 to inhibit secretion of plasminogen activator inhibitor-1 in EGR-1 regulated cells. 1999, *J. Biol. Chem.* 274, 4400–4411. Arteaga et al. used antibodies or antisense oligonucleotides targeted to TGF-β2 to enhance sensitivity of cancer cells to NK cells in the presence of tamoxifen. 1999, *J. Nat. Cancer Inst.* 91, 46–53.

Tzai et al., 1998, *Anticancer Res.*, 18, 1585–1589, used antisense oligonucleotides specific for TGF-β1 to inhibit in vitro and in vivo growth of murine bladder cancer cells.

The role of TGF-β in diabetic nephropathy is reviewed in Hoffman, et al., 1998, Electrolyte Metab., 24, 190–196.

Neutralizing anti-TGF-β antibodies or antisense oligonucleotides directed to TGF-β1 are reported to prevent the hypertrophic effects of high glucose and the stimulation of matrix synthesis in renal cells.

Antisense phosphorothioate oligodeoxynucleotides targeted to TGF-β3 were used by Nakajima et al. (1998, Japan. Dev. Biol, 194, 99–113; abstract only) and others to block transformation of atrioventricular canal endothelial cells into invasive mesenchyme.

Chung et al. (U.S. Pat. No. 5,683,988) disclose and claim particular antisense oligodeoxynucleotides targeted to TGF-β and use of these to inhibit scarring.

SUMMARY OF THE INVENTION

The present invention is directed to antisense compounds, particularly oligonucleotides, which are targeted to a nucleic acid encoding TGF-β, and which modulate the expression of TGF-β. Pharmaceutical and other compositions comprising the antisense compounds of the invention are also provided. Further provided are methods of modulating the expression of TGF-β in cells or tissues comprising contacting said cells or tissues with one or more of the antisense compounds or compositions of the invention. Further provided are methods of treating an animal, particularly a human, suspected of having or being prone to a disease or condition associated with expression of TGF-β by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding TGF-β, ultimately modulating the amount of TGF-β produced. This is accomplished by providing antisense compounds which specifically hybridize with one or more nucleic acids encoding TGF-β. As used herein, the terms "target nucleic acid" and "nucleic acid encoding TGF-β" encompass DNA encoding TGF-β, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of TGF-β. In the context of the present invention, "modulation" means either an increase (stimulation) or a decrease (inhibition) in the expression of a gene product. In the context of the present invention, inhibition is a preferred form of modulation of gene expression and mRNA is a preferred target. Further, since many genes (including TGF-β) have multiple transcripts, "modulation" also includes an alteration in the ratio between gene products, such as alteration of mRNA splice products.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding TGF-β. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding TGF-β, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap.

The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes of cells, tissues and animals, especially humans. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2'-, 3'- or 5'-hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure. However, open linear structures are generally preferred. Within the oligonucleotide structure, the phosphate groups are commonly referred to as forming the internucleoside backbone of the oligonucleotide. The normal linkage or backbone of RNA and DNA is a 3'-5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$CH_3$, O($CH_2$)$_n$O$CH_3$, O($CH_2$)$_n$$NH_2$, O($CH_2$)$CH_3$, O($CH_2$)$_n$ON$H_2$, and O($CH_2$)$_n$ON [($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes an alkoxyalkoxy group, 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486–504). A further preferred modification includes 2'-dimethylaminooxyethoxy, i.e., a O($CH_2$)$_2$ON($CH_3$)$_2$ group, also known as 2'-DMAOE.

Other preferred modifications include 2'-methoxy (2-O—$CH_3$), 2'-aminopropoxy (2'-O$CH_2CH_2CH_2NH_2$) and 2'-fluoro (2-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, each of which is herein incorporated by reference.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858–859, Kroschwitz, J. I., ed. John Wiley & Sons, 1990, those disclosed by Englisch et al., Angewandte Chemie, International Edition, 1991, 30, 613, and those disclosed by Sanghvi, Y. S., Crooke, S. T., and Lebleu, B. eds., Antisense Research and Applications, CRC Press, Boca Raton, 1993, pp. 289–302. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553–6556), cholic acid (Manoharan et al., Bioorg. Med. Chem. Let., 1994, 4, 1053–1060), a thioether, e.g., hexyl-S-tritylthiol (Manoharan et al., Ann. N.Y. Acad. Sci., 1992, 660, 306–309; Manoharan et al., Bioorg. Med. Chem. Let., 1993, 3, 2765–2770), a thiocholesterol (Oberhauser et al., Nucl. Acids Res., 1992, 20, 533–538), an aliphatic chain, e.g., dodecandiol or undecyl residues (Saison-Behmoaras et al., EMBO J., 1991, 10, 1111–1118; Kabanov et al., FEBS Lett., 1990, 259, 327–330; Svinarchuk et al., *Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416, 016; 5,459,127; 5,521,291; 5,543,158; 5,547,932; 5,583, 020; 5,591,721; 4,426,330; 4,534,899; 5,013,556; 5,108, 921; 5,213,804; 5,227,170; 5,264,221; 5,356,633; 5,395, 619; 5,416,016; 5,417,978; 5,462,854; 5,469,854; 5,512, 295; 5,527,528; 5,534,259; 5,543,152; 5,556,948; 5,580, 575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 or in WO 94/26764.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred addition salts are acid salts such as the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embolic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic aci, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of TGF-β is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding TGF-β, enabling sandwich and other assays to easily be constructed to exploit this fact. Hybridization of the antisense oligonucleotides of the invention with a nucleic acid encoding TGF-β can be detected by means known in the art. Such means may include conjugation of an enzyme to the oligonucleotide, radiolabelling of the oligonucleotide or any other suitable detection means. Kits using such detection means for detecting the level of TGF-β in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal, intradermal and transdermal), oral or parenteral. Parenteral administration includes intravenous, intraarterial, subcutaneous, intraperitoneal or intramuscular injection or infusion; or intracranial, e.g., intrathecal or intraventricular, administration. oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and/or formulations comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8, 91–192; Muranishi, *Critical Reviews in Therapeutic Drug Carrier Systems*, 1990, 7, 1–33). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems,* 1991, 8:2, 91–192; Muranishi, *Critical Reviews in Therapeutic Drug Carrier Systems,* 1990, 7:1, 1–33; El-Hariri et al., *J. Pharm. Pharmacol.,* 1992, 44, 651–654). Examples of some presently preferred fatty acids are sodium caprate and sodium laurate, used singly or in combination at concentrations of 0.5 to 5%.

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives. A presently preferred bile salt is chenodeoxycholic acid (CDCA) (Sigma Chemical Company, St. Louis, Mo.), generally used at concentrations of 0.5 to 2%.

Complex formulations comprising one or more penetration enhancers may be used. For example, bile salts may be used in combination with fatty acids to make complex formulations. Preferred combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems,* 1991, 8:2, 92–192; Muranishi, *Critical Reviews in Therapeutic Drug Carrier Systems,* 1990, 7:1, 1–33; Buur et al., *J. Control Rel.,* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems,* 1991, 8:2, 92–191); and perfluorochemical emulsions, such as FC-43 (Takahashi et al., *J. Pharm. Pharmacol.,* 1988, 40, 252–257).

Non-surfactants include, for example, unsaturated cyclicureas, 1-alkyl- and 1-alkenylazacyclo-alkanone derivatives (Lee et al., *Critical Reviews in Therapeutic Drug Carrier Systems,* 1991, 8:2, 92–191); and non-steroidal anti-inflammatory agents such as diclofenac sodium, indomethacin and phenylbutazone (Yamashita et al., *J. Pharm. Pharmacol.,* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.,* 1995, 6, 698–708).

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy*, 15th Ed., Berkow et al., eds., 1987, Rahway, N.J., pp. 1206–1228. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pp. 2499–2506 and 46–49, respectively. Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506, 351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods (Sanghvi, et. al., *Nucleic Acids Research*, 1993, 21, 3197–3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously by Kawasaki, et. al., *J. Med. Chem.*, 1993, 36, 831–841 and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 hours) to give a solid that was crushed to a light tan powder (57 g, 85% crude yield). The NMR spectrum was consistent with the structure, contaminated with phenol as its sodium salt (ca. 5%). The material was used as is for further reactions or purified further by column chromatography using a gradient of methanol in ethyl acetate (10–25%) to give a white solid, mp 222–4° C.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/Acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 hours using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M was dissolved in $CH_2Cl_2$ (1 L) Tetrazole diisopropylamine (7.1 g) and 2-cyanoethoxy-tetra (isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were baceketracted with $CH_2Cl_2$ (300 mL), and the extracts were combined, dried over $MgSO_4$ and concentrated. The residue obtained was chromatographed on a 1.5 kg silica column using EtOAc/Hexane (3:1) as the eluting solvent. The pure fractions were combined to give 90.6 g (87%) of the title compound.

Example 2
Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 seconds and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAS) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-omethyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hours at room temperature is then done to deprotect all bases and sample was again lyophilized to dryness. The pellet is resuspended in 1M TBAF in THF for 24 hours at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O(methoxyethyl)amidites for the 2'-O-methyl amidites.

[2'-O-(2-Methoxyethyl)Phosphodiester]-[2'-deoxy Phosphorothioate]-[2'-O-(2-Methoxyethyl)Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl)amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides were purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides are synthesized via solid phase P(III) phosphoramidite chemistry on an automated synthesizer capable of assembling 96 sequences simultaneously in a standard 96 well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites are purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides are cleaved from support and deprotected with concentrated $NH_4OH$ at elevated temperature (55–60° C.) for 12–16 hours and the released product then dried in vacuo. The dried product is then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well is assessed by dilution of samples and UV absorption spectroscopy. The full-length integrity of the individual products is evaluated by capillary electrophoresis (CE) in either the 96 well format (Beckman P/ACEJ MDQ) or, for individually prepared samples, on a commercial CE apparatus (e.g., Beckman P/ACEJ 5000, ABI 270). Base and backbone composition is confirmed by mass analysis of the compounds utilizing electrospray-mass spectroscopy. All assay test plates are diluted from the master plate using single and multi-channel robotic pipettors. Plates are judged to be acceptable if at least 85% of the compounds on the plate are at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR, RNAse protection assay (RPA) or Northern blot analysis. The following four human cell types are provided for illustrative purposes, but other cell types can be routinely used.

T-24 Cells

The transitional cell bladder carcinoma cell line T-24 is obtained from the American Type Culture Collection (ATCC) (Manassas, Va.). T-24 cells are routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells are routinely passaged by trypsinization and dilution when they reached 90% confluence. Cells are seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 is obtained from the American Type Culture Collection (ATCC) (Manassas, Va.). A549 cells are routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells are routinely passaged by trypsinization and dilution when they reached 90% confluence.

NHDF Cells

Human neonatal dermal fibroblast (NHDF) are obtained from the Clonetics Corporation (Walkersville Md.). NHDFs are routinely maintained in Fibroblast Growth Medium (Clonetics Corporation, Walkersville Md.) supplemented as recommended by the supplier. Cells are maintained for up to 10 passages as recommended by the supplier.

HEK Cells

Human embryonic keratinocytes (HEK) are obtained from the Clonetics Corporation (Walkersville Md.). HEKs are routinely maintained in Keratinocyte Growth Medium (Clonetics Corporation, Walkersville Md.) formulated as recommended by the supplier. Cells are routinely maintained for up to 10 passages as recommended by the supplier.

Treatment with Antisense Compounds

When cells reached 80% confluency, they are treated with oligonucleotide. For cells grown in 96-well plates, wells are washed once with 200 µL OPTI-MEMJ-1 reduced-serum medium (Gibco BRL) and then treated with 130 µL of OPTI-MEMJ-1 containing 3.75 µg/mL LIPOFECTINJ (Gibco BRL) and the desired oligonucleotide at a final concentration of 150 nM. After 4 hours of treatment, the medium is replaced with fresh medium. Cells are harvested 16 hours after oligonucleotide treatment.

Example 10
Analysis of Oligonucleotide Inhibition of TGF-β Expression

Antisense modulation of TGF-β expression can be assayed in a variety of ways known in the art. For example, TGF-β mRNA levels can be quantitated by Northern blot analysis, RNAse protection assay (RPA), competitive polymerase chain reaction (PCR), or real-time PCR (RT-PCR). RNA analysis can be performed on total cellular RNA or poly(A)+ mRNA. Methods of RNA isolation are taught in, for example, Ausubel, et al., Current Protocols in Molecular Biology, Volume 1, John Wiley & Sons, Inc., 1993, pp. 4.1.1–4.2.9 and 4.5.1–4.5.3. Northern blot analysis is routine in the art and is taught in, for example, Ausubel, et al., *Current Protocols in Molecular Biology*, Volume 1, John Wiley & Sons, Inc., 1996, pp. 4.2.1–4.2.9. Real-time quantitative (PCR) can be conveniently accomplished using the commercially available ABI PRISMJ 7700 Sequence Detection System, available from PE-Applied Biosystems, Foster City, Calif. and used according to manufacturer's instructions. Other methods of PCR are also known in the art.

TGF-β protein levels can be quantitated in a variety of ways well known in the art, such as immunoprecipitation, Western blot analysis (immunoblotting), ELISA, flow cytometry or fluorescence-activated cell sorting (FACS). Antibodies directed to TGF-β can be identified and obtained from a variety of sources, such as PharMingen Inc., San Diego Calif., or can be prepared via conventional antibody generation methods. Methods for preparation of polyclonal antisera are taught in, for example, Ausubel, et al., *Current Protocols in Molecular Biology*, Volume 2, John Wiley & Sons, Inc., 1997, pp. 11.12.1–11.12.9. Preparation of monoclonal antibodies is taught in, for example, Ausubel, et al., *Current Protocols in Molecular Biology*, Volume 2, John Wiley & Sons, Inc., 1997, pp. 11.4.1–11.11.5.

Immunoprecipitation methods are standard in the art and can be found at, for example, Ausubel, et al., *Current Protocols in Molecular Biology*, Volume 2, John Wiley & Sons, Inc., 1998, pp. 10.16.1–10.16.11. Western blot (immunoblot) analysis is standard in the art and can be found at, for example, Ausubel, et al., *Current Protocols in Molecular Biology*, Volume 2, John Wiley & Sons, Inc., 1997, pp. 10.8.1–10.8.21. Enzyme-linked immunosorbent assays (ELISA) are standard in the art and can be found at, for example, Ausubel, et al., *Current Protocols in Molecular Biology*, Volume 2, John Wiley & Sons, Inc., 1991, pp. 11.2.1–11.2.22.

Example 11

Poly(A)+ mRNA Isolation

Poly(A)+ mRNA is isolated according to Miura et al., *Clin. Chem.*, 1996, 42, 1758–1764. Other methods for poly(A)+ mRNA isolation are taught in, for example, Ausubel, et al., *Current Protocols in Molecular Biology*, Volume 1, John Wiley & Sons, Inc., 1993, pp. 4.5.1–4.5.3. Briefly, for cells grown on 96-well plates, growth medium is removed from the cells and each well is washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 μL of lysate is transferred to Oligo d(T) coated 96-well plates (AGCT Inc., Irvine Calif.). Plates are incubated for 60 minutes at room temperature, washed 3 times with 200 μL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 μL of elution buffer (5 mM Tris-HCl pH 7.6), preheated to 70° C. is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Example 12

Total RNA Isolation

Total mRNA is isolated using an RNEASY 96J kit and buffers purchased from Qiagen Inc. (Valencia Calif.) following the manufacturer's recommended procedures. Briefly, for cells grown on 96-well plates, growth medium is removed from the cells and each well is washed with 200 μL cold PBS. 100 μL Buffer RLT is added to each well and the plate vigorously agitated for 20 seconds. 100 μL of 70% ethanol is then added to each well and the contents mixed by pipetting three times up and down. The samples are then transferred to the RNEASY 96J well plate attached to a QIAVACJ manifold fitted with a waste collection tray and attached to a vacuum source. Vacuum is applied for 15 seconds. 1 mL of Buffer RW1 is added to each well of the RNEASY 96J plate and the vacuum again applied for 15 seconds. 1 mL of Buffer RPE is then added to each well of the RNEASY 96J plate and the vacuum applied for a period of 15 seconds. The Buffer RPE wash is then repeated and the vacuum is applied for an additional 10 minutes. The plate is then removed from the QIAVACJ manifold and blotted dry on paper towels. The plate is then re-attached to the QIAVACJ manifold fitted with a collection tube rack containing 1.2 mL collection tubes. RNA is then eluted by pipetting 60 μL water into each well, incubating 1 minute, and then applying the vacuum for 30 seconds. The elution step is repeated with an additional 60 μL water.

Example 13

Real-time Quantitative PCR Analysis of TGF-β mRNA Levels

Quantitation of TGF-β mRNA levels is determined by real-time quantitative PCR using the ABI PRISMJ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISMJ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents are obtained from PE-Applied Biosystems, Foster City, Calif. RT-PCR reactions are carried out by adding 25 μL PCR cocktail (1×TAQMANJ buffer A, 5.5 mM MgCl$_2$, 300 μM each of DATP, dCTP and dGTP, 600 μM of dUTP, 100 nM each of forward primer, reverse primer, and probe, 20 Units RNAse inhibitor, 1.25 Units AMPLITAQ GOLDJ, and 12.5 Units MuLV reverse transcriptase) to 96 well plates containing 25 μL poly(A) mRNA solution. The RT reaction is carried out by incubation for 30 minutes at 48° C. Following a 10 minute incubation at 95° C. to activate the AMPLITAQ GOLDJ, 40 cycles of a two-step PCR protocol are carried out: 95° C. for 15 seconds (denaturation) followed by 60° C. for 1.5 minutes (annealing/extension).

Example 14
Antisense Inhibition of Murine TGF-β1

Antisense oligonucleotides were designed to hybridize to the mouse TGF-β1 nucleic acid sequence, using published sequence information (GenBank accession No AJ009862; Locus name MMU009862, provided herein as SEQ ID NO: 1). All oligonucleotides have phosphorothioate backbones and are 2'-methoxyethyl (2'-MOE) gapmers.

TABLE 1

Antisense oligonucleotides targeted to mouse TGF-β1

| ISIS # | Nucleotide sequence[1] (5'--->3') | SITE on TARGET SEQUENCE[2] | SEQ ID NO. |
|---|---|---|---|
| 105193 | TGTCTGGAGGATCCGCGGCG | 49 | 2 |
| 105194 | TGCTCCTTTGCCGGCTCCCA | 149 | 3 |
| 105195 | CGAGACAGCGCAGTGCCAAG | 325 | 4 |
| 105196 | GGCTCCCGAGGGCTGGTCCG | 435 | 5 |
| 105197 | GCAGGAGTCGCGGTGAGGCT | 696 | 6 |
| 105198 | AAAGGTGGGATGCGGAGGCC | 801 | 7 |
| 105199 | CAGTAGCCGCAGCCCCGAGG | 875 | 8 |
| 105200 | AGTCCCGCGGCTGGCCTCCC | 937 | 9 |
| 105201 | GGCTTCGATGCGCTTCCGTT | 992 | 10 |
| 105202 | GGCGGTACCTCCCCCTGGCT | 1057 | 11 |
| 105203 | CGCCTGCCACCCGGTCGCGG | 1119 | 12 |
| 105204 | GTCCACCATTAGCACGCGGG | 1193 | 13 |
| 105205 | GGCACTGCTTCCCGAATGTC | 1282 | 14 |
| 105206 | GTCAGCAGCCGGTTACCAAG | 1411 | 15 |
| 105207 | AGTGAGCGCTGAATCGAAAG | 1515 | 16 |
| 105208 | GATGGTGCCCAGGTCGCCCC | 1598 | 17 |
| 105209 | AGGAGCAGGAAGGGCCGGTT | 1627 | 18 |
| 105210 | TCCGGTGCCGTGAGCTGTGC | 1680 | 19 |
| 105211 | GCCCTTGGGCTCGTGGATCC | 1796 | 20 |
| 105212 | CGCCCGGGTTGTGTTGGTTG | 1896 | 21 |
| 105213 | GGCTTGCGACCCACGTAGTA | 1969 | 22 |
| 105214 | GGCGGGGCTTCAGCTGCACT | 2030 | 23 |
| 110409 | CGCCCGGGTTGTGCTGGTTG | 1896 | 24 |
|  | 1 base mismatch to 105212 |  |  |
| 110410 | GTGCTCCCATTGAAAGCCGG | 1193 | 25 |
|  | 8 base mismatch to 105204 |  |  |

[1]Emboldened residues, 2'-methoxyethoxy- residues (others are 2'-deoxy-). All C residues, including 2'-MOE and 2'- deoxy residues, are 5-methyl-cytosines.
[2]Position of first nucleotide at the target site on GenBank accession No AJ009862; Locus name MMU009862, provided herein as SEQ ID NO: 1).

The antisense compounds in the table above were screened by Northern blot at 200 nM oligonucleotide concentration in mouse bEND3 endothelial cells (see Montesano et al., *Cell*, 1990, 62, 435, and Stepkowski et al., *J. Immunol.*, 1994, 153, 5336). Cells were treated with oligonucleotide (200 nM) and 10 μg/ml of Lipofectin (Life Technologies, Inc., Gaithersburg, Md.) for 4 hours. Cells were then washed and allowed to recover for a further 24 hr. RNA was isolated and TGF-β1 mRNA expression was measured by Northern blotting. The gels were stripped and reprobed for expression of a housekeeping gene (G3PDH) to confirm equal loading. TGF-β1 levels are expressed as a percent of control activity, normalized to G3PDH. Results are shown in Table 2.

TABLE 2

Antisense inhibition of mouse TGF-β1

| ISIS # | % of Control Activity | % Inhibition | SEQ ID NO. |
|---|---|---|---|
| 105193 | 6 | 94 | 2 |
| 105194 | 3 | 97 | 3 |
| 105195 | 20 | 80 | 4 |
| 105196 | 8 | 92 | 5 |
| 105198 | 19 | 81 | 7 |
| 105199 | 69 | 31 | 8 |
| 105200 | 18 | 82 | 9 |
| 105201 | 86 | 14 | 10 |
| 105202 | 209 | — | 11 |
| 105203 | 160 | — | 12 |
| 105204 | 47 | 53 | 13 |
| 105205 | 12 | 88 | 14 |
| 105206 | 11 | 89 | 15 |
| 105207 | 31 | 69 | 16 |
| 105208 | 148 | — | 17 |
| 105209 | 20 | 80 | 18 |
| 105211 | 148 | — | 20 |
| 105212 | 16 | 84 | 21 |
| 105213 | 9 | 91 | 22 |
| 105214 | 10 | 90 | 23 |

Oligonucleotides ISIS 105193, 105194, 105195, 105196, 105198, 105200, 105204, 105205, 105206, 105207, 105209, 105212, 105213 and 105214 gave greater than 50% inhibition of TGF-β1 mRNA in this experiment and are preferred.

Example 15
Dose Response of Antisense Oligonucleotides Targeted to Marine TGF-β1 bEND.3 cells were treated with oligonucleotides at various concentrations with 15 μg/ml Lipofectin for 4 hours, then washed and allowed to recover for 24 hours. TGF-β1 mRNA levels were determined by Northern blot analysis and normalized to G3PDH levels. Results are shown in Table 3.

TABLE 3

Dose response of antisense oligonucleotides targeted to murine TGF-β1

| Oligonucleotide | Dose (nM) | % of Control | % Inhib. |
|---|---|---|---|
| Lipofectin |  | 100 |  |
| ISIS 105195 |  |  |  |
|  | 25 | 47 | 53 |
|  | 50 | 35 | 65 |
|  | 100 | 25 | 75 |
|  | 200 | 18 | 82 |
|  | 300 | 8 | 92 |
| ISIS 105199 |  |  |  |
|  | 25 | 115 | — |
|  | 50 | 126 | — |
|  | 100 | 125 | — |
|  | 200 | 103 | — |
| ISIS 105204 |  |  |  |
|  | 25 | 31 | 69 |
|  | 50 | 22 | 78 |
|  | 100 | 16 | 84 |
|  | 200 | 11 | 89 |
|  | 300 | 11 | 89 |

TABLE 3-continued

Dose response of antisense oligonucleotides targeted to murine TGF-β1

| Oligonucleotide | Dose (nM) | % of Control | % Inhib. |
|---|---|---|---|
| ISIS 105212 | | | |
| | 25 | 43 | 57 |
| | 50 | 29 | 71 |
| | 100 | 26 | 74 |
| | 200 | 18 | 82 |
| | 300 | 24 | 76 |
| ISIS 105214 | | | |
| | 25 | 30 | 70 |
| | 50 | 17 | 83 |
| | 100 | 17 | 83 |
| | 200 | 11 | 89 |
| | 300 | 14 | 86 |

ISIS 105195, 105204, 105212 and 105214 had IC50s below 25 nM in this experiment and are preferred.

Example 16
"Humanized" Mouse TGF-β1 Antisense Oligonucleotide

It was determined by BLAST analysis (Altschul S F et al., *J. Mol. Biol.* 1990, 215, 403–10) that ISIS 105204, designed to target mouse TGF-β1, has only a single mismatch to the human TGF-β1 gene target, and, except for the 5'-most base on the oligonucleotide, is complementary to a site beginning at nucleotide 1167 on the human target (GenBank accession no. X02812; locus name HSTGFB1; Derynck,R., et al., 1985, *Nature* 316, 701–705). An oligonucleotide (TTCCACCATTAGCACGCGGG; ISIS 113849; SEQ ID NO: 26) was designed and synthesized which was a complete match to the human target sequence at this site. This compound is a phosphorothioate backbone with 2'-MOE nucleotides shown in bold. All C residues are 5-methyl C.

Example 17
Efficacy of ISIS 105204 in Rat Kidney Cells

ISIS 105204, designed to target mouse TGF-β1, was tested in rat NRK kidney cells (available from American Type Culture Collection, Manassas Va.). This oligonucleotide has 100% complementarity to the rat TGF-β1 sequence (GenBank accession no.X52498; locus name RNTGFB1, provided herein as SEQ ID NO: 27). A dose response is shown in Table 4. ISIS 105195, which is targeted to a region of the mouse TGF-β1 sequence which shares only 9 of 20 nucleobases with the rat sequence, is shown for comparison.

TABLE 4

Dose response of antisense oligonucleotides targeted to mouse TGF-β1 in rat NRK cells

| ISIS # | Dose (nM) | % of Control activity | % Inhibition | SEQ ID NO |
|---|---|---|---|---|
| Lipofectin | | 100 | — | |
| 105195 | | | | 4 |
| | 100 | 115 | — | |
| | 200 | 98 | 2 | |
| | 300 | 97 | 3 | |

TABLE 4-continued

Dose response of antisense oligonucleotides targeted to mouse TGF-β1 in rat NRK cells

| ISIS # | Dose (nM) | % of Control activity | % Inhibition | SEQ ID NO |
|---|---|---|---|---|
| 105204 | | | | 13 |
| | 50 | 56 | 44 | |
| | 100 | 50 | 50 | |
| | 200 | 39 | 61 | |

Example 18
Effect of Antisense Inhibition of TGF-β1 on Fibrotic Scarring

A model for fibrosis has been developed in which smotic pumps are implanted subcutaneously in rats. ormally the pump becomes encapsulated by fibrotic scar tissue. The effect of antisense inhibition of TGF-β1 on scarring can be analyzed and quantitated.

2 ml Alzet osmotic pumps (Alza corporation, Palo Alto, Calif.) were implanted subcutaneously on the back of female Sprague Dawley rats. Four rats per experimental group were implanted with pumps containing PBS, 5 mgs of TGF-β1 antisense oligonucleotide and 5 mgs of an eight base mismatch control oligonucleotide, ISIS 110410. After 3 weeks the encapsulation tissue surrounding the pump was removed, weighed, snap frozen, and evaluated for TGF-β1 mRNA by Northern blot analysis or RNAse protection assay using the rCK3b template (Pharmingen, San Diego Calif.) and by immunohistochemistry. For the latter, formalin fixed, paraffin embedded tissues were stained with Masson's Trichrome Stain for Collagen and immunochemical localization of oligonucleotide. Frozen tissues were antibody-stained for TGF-β1 (antibody from Santa Cruz Biotechnologies, Santa Cruz, Calif.), and EDA Fibronectin (antibody from Harlan Bioproducts, Sussex, England). The antibodies were detected with secondary reagents directly conjugated to HRP and DAB (brown) was used as the substrate.

TGF-β1 expression in the scar tissue was reduced by reater than 50% after 28-day treatment with ISIS 105204 (oligonucleotide dose 15 mg/kg; and to greater than 30% ith a dose of 5 mg/kg), as measured by Northern blot nalysis of TGF-β1 mRNA levels. This is shown in Table 5.

TABLE 5

Effect of ISIS 105204 on TGF-β1 expression in rat scar tissue

| Oligonucleotide | % of control | % inhibition | SEQ ID NO |
|---|---|---|---|
| Saline control | 100 | — | |
| ISIS 110410 (8-base mismatch of 105204) | 83 | 17 | 25 |
| ISIS 105204 | 44 | 56 | 13 |

Immunohistochemical staining showed that TGF-β1 protein expression is reduced in scar tissue from mice treated with ISIS 105204. Levels of collagen and fibronectin, which are markers for fibrosis, were also reduced in scar tissue from these mice. Staining also showed a decrease in the number of CD18 positive cells.

Example 19
Antisense Oligonucleotides Targeted to Human TGF-β1

Antisense oligonucleotides were designed to hybridize to the human TGF-β1 nucleic acid sequence, using published sequence information; Derynck,R., et al., 1985, Nature 316, 701–705; GenBank accession number X02812; locus name HSTGFB1, incorporated herein as SEQ ID NO: 28. Oligonucleotides have phosphorothioate backbones and are 2'MOE gapmers. Sequences are shown in Table 6.

TABLE 6

Antisense oligonucleotides targeted to human TGF-β

| ISIS # | Nucleotide sequence[1] (5'--->3') | SITE on TARGET SEQUENCE[2] | SEQ ID NO. |
|---|---|---|---|
| 104978 | CGACTCCTTCCTCCGCTCCG | 113 | 29 |
| 104979 | CTCGTCCCTCCTCCCGCTCC | 209 | 30 |
| 104980 | AAGTCCTGCCTCCTCGCGGG | 317 | 31 |
| 104981 | AAGGGTCTAGGATGCGCGGG | 531 | 32 |
| 104982 | CTCAGGGAGAAGGGCGCAGT | 692 | 33 |
| 104983 | GCACTGCCGAGAGCGCGAAC | 802 | 34 |
| 104984 | GTAGCAGCAGCGGCAGCAGC | 862 | 35 |
| 104985 | ATGGCCTCGATGCGCTTCCG | 968 | 36 |
| 104986 | GCGTAGTAGTCGGCCTCAGG | 1136 | 37 |
| 104987 | ACCACTGCCGCACAACTCCG | 1447 | 38 |
| 104988 | TCGGCGGCCGGTAGTGAACC | 1557 | 39 |
| 104989 | GAAGTTGGCATGGTAGCCCT | 1788 | 40 |
| 104990 | GGCGCCCGGGTTATGCTGGT | 1875 | 41 |
| 104991 | CTCCACCTTGGGCTTGCGGC | 1956 | 42 |
| 104992 | AATGACACAGAGATCCGCAG | 2155 | 43 |
| 104993 | TAGATCTAACTACAGTAGTG | 2305 | 44 |
| 104994 | CGCCTGGCCTGAACTACTAT | 2525 | 45 |
| 104995 | CCCAGGCTGGTCTCAAATGC | 2609 | 46 |

[1]Emboldened residues, 2'-methoxyethoxy- residues (others are 2'-deoxy-). All C residues, including 2'-MOE and 2'- deoxy residues, are 5-methyl-cytosines.
[2]Position of first nucleotide at the target site on GenBank accession number X02812; locus name HSTGFB1, provided herein as SEQ ID NO: 28.

Oligonucleotides were screened in 293T human kidney cells at a concentration of 200 nM with 10 μg/ml of Lipofectin for a period of four hours. Cells were washed and allowed to recover for a further 24 hr. At this point RNA was isolated and TGF-β1 mRNA levels were determined by Ribonuclease Protection Assay (RPA) using the hCK-3 template (Pharmingen, San Diego Calif.) according to the manufacturer's instructions. TGF-β1 mRNA levels were normalized to GAPDH and expressed as a percentage of untreated control. Results are shown in Table 7.

TABLE 7

Antisense Inhibition of Human TGF-β1

| ISIS # | % of Control Activity | % Inhibition | SEQ ID NO: |
|---|---|---|---|
| 104978 | 150 | — | 29 |
| 104979 | 94 | 6 | 30 |
| 104980 | 82 | 18 | 31 |
| 104981 | 86 | 14 | 32 |
| 104982 | 94 | 6 | 33 |
| 104983 | 52 | 48 | 34 |
| 104985 | 59 | 41 | 36 |
| 104986 | 59 | 41 | 37 |
| 104987 | 63 | 37 | 38 |
| 104988 | 71 | 29 | 39 |
| 104989 | 86 | 14 | 40 |
| 104990 | 57 | 43 | 41 |

TABLE 7-continued

Antisense Inhibition of Human TGF-β1

| ISIS # | % of Control Activity | % Inhibition | SEQ ID NO: |
|---|---|---|---|
| 104991 | 52 | 48 | 42 |
| 104992 | 47 | 53 | 43 |
| 104993 | 84 | 16 | 44 |
| 104994 | 60 | 40 | 45 |
| 104995 | 64 | 36 | 46 |
| 105204 | 23 | 77 | 13 |

In this experiment ISIS 104983, 104985, 104986, 104990, 104991, 104992, 104994 and 105204 gave at least 40% inhibition of human TGF-β1 mRNA and are preferred. ISIS 104992 and 105204 gave over 50% inhibition.

Example 20
Dose Responses of Antisense Oligonucleotides Targeted to Human TGF-β1

ISIS 113849, 105204, 110410 (8 base mismatch of 105204) and 104992 were tested at 50, 100 and 200 nM for ability to inhibit TGF-β1 mRNA levels. Results are shown in Table 8.

TABLE 8

Dose response of oligonucleotides targeted to human TGF-β1

| ISIS # | Dose (nM) | % of Control Activity | % Inhibition | SEQ ID NO: |
|---|---|---|---|---|
| 104992 | 50 | 65 | 35 | 43 |
|  | 100 | 68 | 32 |  |
|  | 200 | 93 | 7 |  |
| 105204 | 50 | 31 | 69 | 13 |
|  | 100 | 16 | 84 |  |
|  | 200 | 23 | 77 |  |
| 110410 | 50 | 85 | 15 | 25 |
|  | 100 | 64 | 36 |  |
|  | 200 | 50 | 50 |  |
| 113849 | 50 | 29 | 71 | 26 |
|  | 100 | 24 | 76 |  |
|  | 200 | 36 | 64 |  |

ISIS 105204 and 113849 had IC50s below 50 nM in this experiment. These oligonucleotides were found to have little effect on TGF-β2 or TGF-β3 mRNA levels.

Example 21
Antisense Compounds Targeted to Murine TGF-β2

Antisense oligonucleotides were designed to hybridize to the mouse TGF-β2 nucleic acid sequence, using published sequence information from GenBank accession number X57413; Miller, D. A., et al., Mol. Endocrinol. 1989, 3, 1108–1114; locus name MMTGFB2, incorporated herein as SEQ ID NO: 47. The oligonucleotides are shown in Table 9.

TABLE 1

Antisense oligonucleotides targeted to murine TGF-β1

| ISIS # (5'--->3') | Nucleotide sequence[1] | SITE on TARGET SEQUENCE[2] | SEQ ID NO. |
|---|---|---|---|
| 104996 | GCCGGCAGTTTCAGCAGCTC | 34 | 48 |
| 104997 | CTCGCACCCTTCCCTAGCTT | 259 | 49 |

TABLE 1-continued

Antisense oligonucleotides targeted to murine TGF-β1

| ISIS # | Nucleotide sequence[1] (5'-->3') | SITE on TARGET SEQUENCE[2] | SEQ ID NO. |
|---|---|---|---|
| 104998 | TTTCTTGCTCCAGGCGGCCA | 362 | 50 |
| 104999 | GAGCAGGCGGCGAGGATCCC | 493 | 51 |
| 105000 | GCCCTGCCTTCCACACGTGT | 671 | 52 |
| 105001 | GTGCGGAGTGGCTGATCTGA | 830 | 53 |
| 105002 | AAAATGCAACGCGTTCCCAA | 1016 | 54 |
| 105003 | CCGGGACCAGATGCAGGAGC | 1247 | 55 |
| 105004 | TCCGGCTTGCCTTCTCCTGC | 1451 | 56 |
| 105005 | GGGTTTTGCAAGCGGAAGAC | 1668 | 57 |
| 105006 | CGATGTAGCGCTGGGTGGGA | 1754 | 58 |
| 105007 | GGTCTTCCCACTGGTTTTTT | 2032 | 59 |
| 105008 | AAGCTTCGGGATTTATGGTG | 2321 | 60 |
| 105009 | ACCGTGATTTTCGTGTCCTG | 2478 | 61 |
| 105010 | GCGGGCTGGAAACAATACGT | 2854 | 62 |
| 105011 | CCCCTGGCTTATTTGAGTTC | 3075 | 63 |
| 105012 | ACCGGCTTGCTTAAACTGGC | 3297 | 64 |
| 105013 | CAGCCACTTCACGGTCAAAA | 3352 | 65 |
| 105014 | ATGGACCCAGGTAGCTCATG | 3753 | 66 |
| 105015 | CACCCGCCACATGACTCACA | 3874 | 67 |
| 105016 | TACACCCCATGAGCACCAAA | 4097 | 68 |

[1]Emboldened residues, 2'-methoxyethoxy- residues (others are 2'-deoxy-). All C residues, including 2'-MOE and 2'- deoxy residues, are 5-methyl-cytosines.
[2]Position of first nucleotide at the target site on GenBank accession number X57413; Miller, D.A., et al., Mol. Endocrinol. 1989, 3, 1108-1114; locus name MMTGFB2, incorporated herein as SEQ ID NO: 47.

The oligonucleotides shown in Table 9 were screened for the ability to inhibit mouse TGF-β2 mRNA expression by ribonuclease protection assay (RPA) in mouse R6 +/+ fibroblast cells. Cells were treated with oligonucleotide (200 nM) and 10 μg/ml of Lipofectin (Life Technologies, Inc.) for 4 hours. Cells were then washed and allowed to recover for a further 24 hours. RNA was isolated and TGF-β2 mRNA expression was measured by RPA using the mCK3b template (Pharmingen, Inc., San Diego Calif.) according to manufacturer's directions. Results were normalized to GAPDH and expressed as a percent of RNA levels in untreated control cells. Results are shown in Table 10.

TABLE 10

Antisense inhibition of mouse TGF-β2 mRNA expression

| ISIS # | % of control activity | % inhibition | SEQ ID NO: |
|---|---|---|---|
| 104996 | 83 | 17 | 48 |
| 104997 | 79 | 21 | 49 |
| 104998 | 70 | 30 | 50 |
| 104999 | 90 | 10 | 51 |
| 105000 | 64 | 36 | 52 |
| 105001 | 37 | 63 | 53 |
| 105002 | 51 | 49 | 54 |
| 105003 | 28 | 72 | 55 |
| 105004 | 52 | 48 | 56 |
| 105005 | 77 | 23 | 57 |
| 105006 | 53 | 47 | 58 |
| 105007 | 60 | 40 | 59 |
| 105008 | 55 | 45 | 60 |
| 105009 | 28 | 72 | 61 |
| 105010 | 27 | 73 | 62 |
| 105011 | 48 | 52 | 63 |
| 105012 | 35 | 65 | 64 |
| 105013 | 40 | 60 | 65 |
| 105014 | 43 | 57 | 66 |
| 105015 | 64 | 36 | 67 |
| 105016 | 89 | 11 | 68 |

ISIS 105001, 105002, 105003, 105004, 105006, 105008, 105009, 105010, 105011, 105012, 105013 and 105014 gave at least about 45% inhibition of TGF-β2 mRNA expression in this experiment and are preferred. Of these, ISIS 105003, 105009 and 105010 gave at least 70% inhibition.

Interestingly, it was found that oligonucleotides that reduced TGF-β2 also reduced TGF-β3 mRNA levels. This is shown in Table 11.

TABLE 11

Common inhibition of murine TGF-β2 and TGF-β3 by antisense oligonucleotides targeted to murine TGF-β2

| ISIS # | % inhibition of TGF-β2 | % inhibition of TGF-β3 | SEQ ID NO: |
|---|---|---|---|
| 104996 | 17 | 3 | 48 |
| 104997 | 21 | 11 | 49 |
| 104998 | 30 | — | 50 |
| 104999 | 10 | 14 | 51 |
| 105000 | 36 | 16 | 52 |
| 105001 | 63 | 48 | 53 |
| 105002 | 49 | 23 | 54 |
| 105003 | 72 | 67 | 55 |
| 105004 | 48 | 49 | 56 |
| 105005 | 23 | 20 | 57 |
| 105006 | 47 | 60 | 58 |
| 105007 | 40 | 29 | 59 |
| 105008 | 45 | 23 | 60 |
| 105009 | 72 | 55 | 61 |
| 105010 | 73 | 49 | 62 |
| 105011 | 52 | 57 | 63 |
| 105012 | 65 | 42 | 64 |
| 105013 | 60 | 55 | 65 |
| 105014 | 57 | 43 | 66 |
| 105015 | 36 | 52 | 67 |
| 105016 | 11 | 12 | 68 |

Example 22
Reduction in Peritoneal Adhesions by Antisense Inhibition of TGF-β1

The surface of the peritoneal cavity and the enclosed organs are coated with a layer of mesothelial cells that are easily damaged by injury or infection. Following injury (surgery, for example), adhesions form which cause permanent scarring. This scarring can result in bowel obstruction, pain, and/or female infertility. A rat model for peritoneal adhesions has been developed (Williams et al., 1992, J. Surg. Res. 52, 65–70). Animal models have demonstrated that TGF-β promotes the formation of postoperative pelvic adhesions.

In these experiments bilateral uterine injuries were created in 250 gm Sprague Dawley rats by cautery, scraping and crushing. Rats then received 5 mg (20 mg/kg) of an antisense oligonucleotide (ISIS 105204), 5 mg of a scrambled control oligonucleotide (ISIS 110410) or 1 mL of saline vehicle via intraperitoneal injection.

Uterine adhesions were then graded by masked evaluators using a clinical scale of 0–3 on days 3, 7 and 14 after injury.

In order to localize the target tissue of the antisense oligonucleotides, an additional group of rats were injected with a reporter oligonucleotide and biopsies were perfomed on the uterus, liver and kidney of the treated animals. The tissues were then fixed and the reporter oligonucleotide was immunolocalized with a specific antibody. The reporter oligonucleotide was concentrated heavily in the area of uterine injury at 2 hours and persisted in uterine cells at 72 hours indicating that the oligonucleotide does localize to the injured area.

A single dose of the antisense oligonucleotide (ISIS 105204) to TGF-β1 significantly reduced the severity of peritoneal adhesions, from a mean of 3.0 for control animals to 1.2 for antisense treated animals. A scrambled control oligonucleotide (ISIS 110410) gave a mean adhesion score of 2.4 over the entire study.

Example 23
Effect of Antisense Inhibition of TGF-β1 on Lung Fibrosis

A model of lung fibrosis has been developed using bleomycin to induce pulmonary fibrosis in mice. Wild, J S, S N Giri et al., 1996, Exp. Lung Res. 22, 375–391. Mice receive an intratracheal dose of bleomycin (0.125 U/mouse) or saline, followed by treatment with antisense oligonucleotide (i.p.) over 2 weeks. Mice were treated with ISIS 105204 or 110410. RNA was isolated from lungs and TGF-β1 mRNA levels were determined for mice treated with saline or bleomycin alone, saline or bleomycin plus ISIS 105204, and bleomycin plus the scrambled control ISIS 110410. Results are shown in Table 12. These studies showed a significant reduction of bleomycin-induced lung hydroxyproling content, prolyly hydroxylase and lipid peroxidation. Lung histopathology showed fibrotic lesions to be reduced in bleomycin treated animals receiving the TGF-β1 oligonucleotide compared to saline or mismatch treated animals. Also, RPA (ribonuclease protection assay) analysis revealed a 45% reduction in TGF-β1 RNA in animals treated with ISIS 105204.

TABLE 12

Effect of antisense inhibition of TGF-β1 on lung fibrosis

| Treatment | % of control | % inhibition |
| --- | --- | --- |
| Saline | 100 | — |
| Saline + 105204 | 81 | 19 |
| Bleomycin | 70 | 30 |
| Bleomycin + 110410 | 73 | 27 |
| Bleomycin + 105204 | 37 | 63 |

Example 24
Effect of Antisense Inhibition of TGF-β1 on Conjunctival Scarring Animal models for a variety of fibrotic diseases and conditions exist. Conjunctival scarring is a major predictor of visual prognosis in a variety of eye conditions, including post-surgical healing. For example, the most common cause of failure of glaucoma filtration surgery is scarring at the bleb and sclerostomy sites. A model of conjunctival scarring in the mouse eye has been developed to investigate potential determinants, modes of prevention and treatments for con-junctival scarring. Reichel et al., 1998, Br. J. Ophthalmol. 82, 1072–1077. This model is used to evaluate the effects of locally or systemically delivered antisense to TGF-β on conjunctival scarring.

Alternatively, antisense compounds can be administered at the time of trabeculectomy filtration surgery. Animals are anesthetized, and the general glaucoma filtration trabeculectomy procedure is followed. A conjunctival flap is raised and a viscoelastic solution (e.g., Healon) is injected into the anterior chamber. A paracentesis stab incision is made using a 75 Beaver blade into the anterior chamber. A sclerotomy is performed through the paracentesis incision using a membrane punch and a peripheral iridectomy is done through the sclerostomy. The conjunctival flap is repositioned and closed with suture in two layers. Oligonucleotide solution (100 μl of 40 μM in the case of rabbits, less in mouse or rat) is injected into the bleb by tunneling a 30 gauge needle through the conjunctiva adjacent to the bleb. Animals are sacrificed 24 hours after treatment and eyes are fixed and examined histologically for collagen, fibronectin, and immunohistochemically for TGF-β.

In these experiments Balb-c mice, a highly inbred strain of mice used to produce monoclonal antibodies, were randomly allocated to one of five treatment groups; subconjunctival injection (5 μl) of 25 μg or 12.5 μg of either a TGF-β1 antisense oligonucleotide (ISIS 105204) or a scrambled control oligonucleotide (ISIS 110410), or the carrier saline control. Cellular distribution of oligonucleotide in glaucoma surgery was assessed following subconjunctival administration of a reporter oligonucleotide into the filtration bleb immediately after surgery in NZW rabbits. Mice and rabbits were assessed clinically and enucleated eyes were analyzed at set time intervals histologically.

At days 3 and 7 mouse eyes (n=4) showed significantly reduced white cell infiltration and collagen fibril deposition in the TGF-β1 oligonucleotide treated groups compared to controls. There was also a significant decrease in localization of fibroblasts and elastin related fibers on days 3, 7 and 14 in groups treated with the TGF-β1 antisense oligonucleotide.

At 7 days mouse eyes (4 eyes/treatment group) showed significantly reduced (p<0.05) conjunctival scar formation in the TGF-β1 treated animals as compared to the control group.

The cellular profile suggested that TGF-β1 oligonucleotide delayed the development of the wound healing response. Immunohistochemical staining with an antibody specific for the reporter oligonucleotide in rabbit eyes revealed intense and localized staining of the TGF-β1 oligonucleotide to fibroblasts, epithelial cells and macrophages in the sclera and conjunctiva at the surgical site.

Example 25
Effect of Antisense Inhibition of TGF-β1 on Inflammation-human Skin Xenograft Model in the SCID Mouse Another model used to investigate the processes of inflammation and scarring involves the use of SCID mice transplanted with human skin. SCID mice lack an enzyme necessary to fashion an immune system and can therefore be converted into a model of the human immune system when injected with human cells or tissues. In these experiments human skin (2 cm$^2$) from various surgical procedures (breast reductions or neonatal foreskin) or from cadavers was transplanted onto the side of SCID mice with sutures or surgical staples. After four to six weeks, the mice were bled and tested for Ig to ensure the SCID lineage. After 8 to 10 weeks, the xenograft skin was treated with antisense oligonucleotide, ISIS 105204, SEQ ID NO: 13) in a cream formulation at 48, 24, and 4 hours prior to the injection of 4000 U of tumor necrosis factor-alpha (TNF-α). Levels of TGF-β protein were then assayed in the epidermis and dermis of the xenograft skin by immunohistochemical staining 24 hours after TNF-α injection. Levels were reported as a percentage of the area showing positive staining for the presence of TGF-β protein.

In the epidermis, 3% of the area showed positive staining after treatment with TGF-β antisense oligonucleotide relative to basal levels of 50% and levels of 37% for the placebo cream group. This data was shown to be statistically significant (P=0.0001).

In the dermis, TGF-β levels were below 0.5% with basal levels at 2.5% and placebo cream group levels of 2%.

What is claimed is:

1. An antisense compound 8 to 50 nucleobases in length targeted to a nucleic acid molecule encoding TGF-β1, wherein said antisense compound comprises at least an 8 nucleobase portion of a sequence selected from the group consisting of SEQ ID NO: 2, 3, 4, 5, 7, 9, 13, 14, 15, 18, 21, 22, 23, 37, 43 and 45 and wherein said antisense compound inhibits the expression of TGF-β1.

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage of the antisense oligonucleotide is a phosphorothioate linkage.

5. The compound of claim 2 wherein the antisense oligonucleotide comprises at least one modified sugar moiety.

6. The compound of claim 5 wherein the modified sugar moiety of the antisense oligonucleotide is a 2'-O-methoxyethyl sugar moiety.

7. The compound of claim 2 wherein the antisense oligonucleotide comprises at least one modified nucleobase.

8. The compound of claim 7 wherein the modified nucleobase of the antisense oligonucleotide is a 5-methylcytosine.

9. The compound of claim 2 wherein the antisense oligonucleotide is a chimeric oligonucleotide.

10. A composition comprising the compound of claim 1 and a pharmaceutically acceptable carrier or diluent.

11. The composition of claim 10 further comprising a colloidal dispersion system.

12. The composition of claim 10 wherein the compound is an antisense oligonucleotide.

13. A method of inhibiting the expression of TGF-β1 in cells or tissues comprising contacting said cells or tissues with the compound of claim 1 so that expression of TGF-β1 is inhibited.

14. A method of treating an animal having a disease or condition selected from the group consisting of fibrotic scarring, peritoneal adhesions, lung fibrosis and conjunctival scarring comprising administering to said animal a therapeutically or prophylactically effective amount of the compound of claim 1 so that expression of TGF-β1 is inhibited.

* * * * *